US010091999B2

(12) United States Patent
Arai et al.

(10) Patent No.: US 10,091,999 B2
(45) Date of Patent: Oct. 9, 2018

(54) AGROCHEMICAL COMPOSITION FOR FOLIAGE TREATMENT

(71) Applicant: KUMIAI CHEMICAL INDUSTRY CO., LTD., Tokyo (JP)

(72) Inventors: Hirokazu Arai, Tokyo (JP); Yukiko Nakajima, Tokyo (JP); Toshihiro Ikeuchi, Tokyo (JP); Atsushi Sato, Tokyo (JP)

(73) Assignee: KUMIAI CHEMICAL INDUSTRY CO., Tokyo (JP)

( * ) Notice: Subject to any disclaimer, the term of this patent is extended or adjusted under 35 U.S.C. 154(b) by 0 days.

(21) Appl. No.: 15/121,817

(22) PCT Filed: Feb. 25, 2015

(86) PCT No.: PCT/JP2015/055348

§ 371 (c)(1),
(2) Date: Aug. 26, 2016

(87) PCT Pub. No.: WO2015/129729

PCT Pub. Date: Sep. 3, 2015

(65) Prior Publication Data

US 2017/0006870 A1 Jan. 12, 2017

(30) Foreign Application Priority Data

Feb. 28, 2014 (JP) ................................. 2014-039836

(51) Int. Cl.
*A01N 43/80* (2006.01)
*A01N 25/28* (2006.01)
*A01N 57/20* (2006.01)

(52) U.S. Cl.
CPC ............. *A01N 43/80* (2013.01); *A01N 25/28* (2013.01); *A01N 57/20* (2013.01)

(58) Field of Classification Search
None
See application file for complete search history.

(56) References Cited

U.S. PATENT DOCUMENTS 6,015,773 A 1/2000 Wysong et al.
8,962,525 B2 * 2/2015 Martin .................. A01N 25/22 504/134
2007/0259786 A1 11/2007 Plant et al.
2009/0082206 A1 3/2009 Ikeuchi et al.
2012/0035052 A1 * 2/2012 Kobayashi ............ A01N 43/80 504/101
2013/0130910 A1 5/2013 Hori et al.

FOREIGN PATENT DOCUMENTS

EP 2 371 218 10/2011
EP 2 420 484 2/2012
JP 8-99805 4/1996
JP 9-249505 9/1997
JP 11-512097 10/1999
JP 2007-535513 12/2007
WO WO-2005104848 A1 * 11/2005 ............ A01N 43/80
WO WO-2010119791 A1 * 10/2010 ............ A01N 43/80
WO 2013/059288 4/2013

OTHER PUBLICATIONS

Extended European Search Report dated Jul. 12, 2017 in European Application No. 15754636.7.
International Search Report dated Apr. 28, 2015 in International Application No. PCT/JP2015/055348.
Koishi et al., "Development and Application of the micro/nano Fabrication System of Capsules and Fine Particles", Aug. 31, 2003, CMC Publishing Co., Ltd., Entire Text, with English translation of the relevant part (pp. 212, lines 12-28).
Edited by Pesticide Science Society of Japan, "Guide for Pesticide Preparation", (Noyaku Seizai Guide), 1997, pp. 173-182, with English translation of the relevant part (p. 173, 5th line from the bottom, table 2; p. 178, 5th lines from the bottom to p. 179).
Singh et al., "Microencapsulation: a promising technique for controlled drug delivery", Research in Pharmaceutical Sciences, 5(2):65-77 (2010).
Opposition to Grant of Invention Patent received Jun. 5, 2017 in Costa Rican Application No. 2016-0442.
Columbian Patent Office Action, dated Jul. 19, 2018, in corresponding Columbian Patent Application No. NC2016/0001866.

* cited by examiner

*Primary Examiner* — Alton N Pryor
(74) *Attorney, Agent, or Firm* — Wenderoth, Lind & Ponack, L.L.P.

(57) ABSTRACT

Provided is an agrochemical composition for foliage treatment, which does not cause phytotoxicity to a cultivated crop due to adhesion thereto when foliage treatment of an upland field is performed with pyroxasulfone, but has a high level of safety and an herbicidal effect on a broad spectrum of weeds. The agrochemical composition for foliage treatment comprises pyroxasulfone and a masking material that masks the pyroxasulfone, wherein the pyroxasulfone is microencapsulated in or coated with the masking material such that phytotoxicity to a cultivated crop due to adhesion thereto when foliage spraying is performed is avoided.

12 Claims, No Drawings

AGROCHEMICAL COMPOSITION FOR FOLIAGE TREATMENT

TECHNICAL FIELD

The present invention relates to an agrochemical composition for foliage treatment, which can reduce or prevent phytotoxicity caused by foliage treatment as well as can maintain the effectiveness thereof for a long period.

BACKGROUND ART

Pyroxasulfone shows a high level of herbicidal effect on weeds of Poaceae family, including *Echinochloa crus-galli* var. *caudata, Digitaria ciliaris, Setaria viridis, Poa annua, Sorghum halepense, Alopecurus myosuroides, Lolium multiflorum* (Italian ryegrass), *Lolium rigidum* (rigid ryegrass), *Avena fatua, Beckmannia syzigache,* wild oat and the like; as well as weeds with broad leaves, including *Persicaria lapathifolia, Amaranthus viridis, Chenopodium album, Stellaria media* Stellaria, *Abutilon avicennae, Sida spinosa, Sesbania exaltata, Ambrosia artemisiifolia, Ipomoea nil, Galium spurium* var. *echinospermon, Veronica persica, Veronica hederifolia, Lamium amplexicaule, Viola mandshurica* and the like; and perennial and annual weeds of Cyperaceae family, including *Cyperus rotundus, Cyperus esculentus, Kyllinga brevifolia* Rottb. var. *leiolepis, Cyperus microiria, Cyperus iria* and the like. Moreover, pyroxasulfone is known to have a herbicidal effect on a broad spectrum of weeds.

However, when pyroxasulfone is used at an upland field for foliage treatment, it sometimes causes phytotoxicity to useful crops and useful plants such as fruit trees, vegetables, flowering plants, and trees, including *Triticum aestivum, Hordeum vulgare, Secale cereale, Zea mays, Sorghum bicolor, Glycine max, Brassica rapa, Carthamus tinctorius, Helianthus annuus, Linum usitatissimum, Arachis hypogaea, Sesamum indicum, Solanum tuberosum, Ipomoea batatas, Allium cepa, Allium sativum, Beta vulgaris,* cotton plants, mint plants, lawn plants and the like, so that the usage of pyroxasulfone had been limited to soil treatment.

Because of this, an agrochemical composition for foliage treatment at an upland field having a high level of safety to those useful crops and useful plants and a herbicidal effect on a broad spectrum of weeds had been desired as an agrochemical active ingredient comparable to pyroxasulfone.

On the other hand, a microencapsulation technology for agrochemical active ingredients is known and, for example, Non-patent Documents 1 discloses microcapsules of various useful chemical compounds, including an agrochemical active ingredient, which microcapsules use different types of materials for their wall members, and the manufacturing procedure thereof.

However, microencapsulation of an agrochemical active ingredient has conventionally aimed in general to control dissolution of the agrochemical active ingredient. Because dissolution of an agrochemical active ingredient from an agrochemical composition, including dissolution of an agrochemical active ingredient from microcapsules, is always mediated through water in a farm field, the microencapsulation of an agrochemical active ingredient has been considered to be a useful technology in an environment, such as paddy field, which is rich in water. Accordingly, the microencapsulation of an agrochemical active ingredient has been considered so far to be difficult to be technically applicable to a farm field, such as upland field, which is short of water.

That is, there has been heretofore little knowledge of an agrochemical composition, which has been microencapsulated intended for a phenomenon other than dissolution control, and particularly any formulation technology, which also enables foliage treatment by microencapsulation of pyroxasulfone applicable for soil treatment has not been known at all.

RELATED ART DOCUMENT

Non-Patent Document

Non-patent Document 1: Koishi et al., "Development and Application of the micro/nano Fabrication System of Capsules and Fine Particles" Aug. 31, 2003, CMC Publishing Co., Ltd., Entire text.

SUMMARY OF THE INVENTION

Problems to be Solved by the Invention

The object of the present invention is to provide an agrochemical composition for foliage treatment, which does not cause phytotoxicity to a cultivated crop due to adhesion thereto when foliage treatment of an upland field is performed with pyroxasulfone, but has a high level of safety and a herbicidal effect on a broad spectrum of weeds.

Means for Solving the Problems

The inventors have intensively studied to solve the problem and eventually found that the above-described problem can be solved by microencapsulating or coating pyroxasulfone with a masking material to establish a structure, which prevents exposure of pyroxasulfone, wherein the masking effect of the masking material on pyroxasulfone is effective when foliage spraying is performed and subsequently is impaired quickly, so that the masking effect is temporarily achieved, thereby completing the present invention.

That is, the present invention includes the following contents:

(1) an agrochemical composition for foliage treatment comprising pyroxasulfone and a masking material that masks the pyroxasulfone, wherein the pyroxasulfone is microencapsulated in or coated with the masking material such that phytotoxicity to a cultivated crop due to adhesion thereto when foliage spraying is performed is avoided;

(2) the agrochemical composition for foliage treatment according to the above-described (1), wherein crystal particles of the pyroxasulfone are directly coated with the masking material;

(3) the agrochemical composition for foliage treatment according to the above-described (1), wherein the pyroxasulfone is microencapsulated by being enclosed or included in the wall member of the masking material;

(4) the agrochemical composition for foliage treatment according to any one of the above-described (1) to (3), wherein the masking material has an average particle size in the range of 0.1 to 150 μm;

(5) the agrochemical composition for foliage treatment according to any one of the above-described (1) to (4), wherein a ratio of the masking material to the pyroxasulfone is in the range of 0.1 to 50 parts by mass relative to 1 part by mass of the pyroxasulfone;

(6) the agrochemical composition for foliage treatment according to any one of the above-described (1) to (5), wherein the masking material is selected from the group consisting of polyurea, polyurethane, polyamide, polyester, ethylcellulose, poly(meth)acrylate-based copolymers, carnauba wax, montanic ester wax, hardened oils and fats, polylactic acid, gelatin, cross-linked melamine, polystyrene, polystyrene-based copolymers, wax, yeast cell wall, alginate, polyglycolic acid, polyethylene glycol-based copolymers and shellac;

(7) the agrochemical composition for foliage treatment according to any one of the above-described (1) to (6), which is in a dosage form of a dust powder, granule, wettable powder, water-dispersible granule, aqueous suspension concentrate, or oil-based suspension concentrate;

(8) the agrochemical composition for foliage treatment according to any one of the above-described (1) to (7), wherein a concentration $K_{24}$ is equal to or less than twice a solubility of pyroxasulfone in water and a concentration $K_1$ is equal to or less than 55% of the concentration $K_{24}$, wherein the concentrations $K_1$ and $K_{24}$ are obtained by measuring a concentration of pyroxasulfone in water 1 hour and 24 hours after a pre-determined amount of the agrochemical composition for foliage treatment is added to water at 20° C., respectively;

(9) the agrochemical composition for foliage treatment according to any one of the above-described (1) to (8), which further comprises an agrochemical active ingredient other than pyroxasulfone;

(10) the agrochemical composition for foliage treatment according to the above-described (9), wherein the agrochemical active ingredient other than pyroxasulfone is glyphosate or glufosinate;

(11) a method of performing foliage treatment, wherein the agrochemical composition for foliage treatment according to any one of the above-described (1) to (10) is used in combination with an agrochemical active ingredient other than pyroxasulfone;

(12) a method of controlling a pest, comprising spraying the agrochemical composition for foliage treatment according to any one of the above-described (1) to (11) on foliage over an upland field where a cultivated crop in the growing period thereof is growing;

(13) the method for controlling a pest according to the above-described (12), wherein the cultivated crop is *Triticum aestivum, Hordeum vulgare, Secale cereale, Zea mays, Sorghum bicolor, Glycine max, Brassica rapa, Carthamus tinctorius, Helianthus annuus, Linum usitatissimum, Arachis hypogaea, Sesamum indicum, Solanum tuberosum, Ipomoea batatas, Allium cepa, Allium sativum, Beta vulgaris,* cotton plants, mint plants, or lawn plants.

Effects of the Invention

According to the present invention, an agrochemical composition for foliage treatment is provided, which does not cause phytotoxicity to a cultivated crop due to adhesion thereto when foliage treatment of an upland field is performed with pyroxasulfone, but has a high level of safety and a herbicidal effect on a broad spectrum of weeds.

MODE FOR CARRYING OUT THE INVENTION

The agrochemical composition for foliage treatment in the present invention is an agrochemical composition for foliage treatment comprising pyroxasulfone and a masking material that masks the pyroxasulfone, wherein the pyroxasulfone is microencapsulated in or coated with the masking material to provide a structure, which prevents exposure of pyroxasulfone, such that phytotoxicity to a cultivated crop due to adhesion thereto when foliage spraying is performed is avoided. Such an agrochemical composition for foliage treatment is produced by, for example, a method in which crystal particles of pyroxasulfone are directly coated with a film of resin, a method in which pyroxasulfone is microencapsulated by being enclosed or included in a wall member made of a resin, or the like.

For the masking material used in the agrochemical composition for foliage treatment in the present invention, known materials are arbitrarily used, and specific examples of the usable material are described, for example, in the above-described Non-patent Document 1. Particularly, polyurea, polyurethane, polyamide, polyester, ethylcellulose, poly(meth)acrylate-based copolymers, carnauba wax, montanic ester wax, hardened oils and fats, polylactic acid, gelatin, cross-linked melamine, polystyrene, polystyrene-based copolymers, wax, yeast cell wall, alginate, polyglycolic acid, polyethylene glycol-based copolymers and shellac are preferably used. The combination ratio of the masking material for pyroxasulfone in the agrochemical composition for foliage treatment is not particularly limited but is preferably 0.1 to 50 parts by mass relative to 1 part by mass of the pyroxasulfone. Such a range is preferable since phytotoxicity to a cultivated crop due to adhesion thereto when foliage spraying is performed is avoided and the masking effect of the masking material is quickly diminished after spraying.

The method in which crystal particles of pyroxasulfone are directly coated with a film of resin includes, for example, a method in which the composition is produced by blending pyroxasulfone and a resin melted by heating or dissolved in a solvent and subsequently cooling the resulted mixture to harden the resin.

The above method may be performed under the presence of an adjuvant capable of imparting rubber elasticity to the composition, such as, for example, hybrid silicone powder and silicone rubber powder.

The method in which pyroxasulfone is microencapsulated by being enclosed or included in a wall member made of a resin includes, for example, a method in which a first solution, which is a volatile hydrophobic solution comprising pyroxasulfone in the non-crystalline state and a resin, is added to a second solution, which is an aqueous solution comprising a water-soluble polymer and a water-soluble active hydrogen-containing compound, and subsequently the resulted mixture is stirred at a high speed and then heated so as to allow the hydrophobic solvent in the first solution to evaporate, thereby obtaining microcapsules in which pyroxasulfone has been included in the matrix made of the resin.

Alternatively, the method includes, for example, a method in which a first reaction solution comprising pyroxasulfone in the crystalline state, a hydrophobic polyisocyanate and a volatile hydrophobic solvent is added to a second reaction solution, which is an aqueous solution comprising a water-soluble polymer and a water-soluble active hydrogen-containing compound, and subsequently the resulted mixture is stirred at a high speed and then heated so as to allow the hydrophobic polyisocyanate, the water-soluble polymer and the water-soluble active hydrogen-containing compound to react while evaporating the hydrophobic solvent in the first solution, thereby obtaining microcapsules in which pyroxasulfone has been enclosed in the wall member made of polyurethane or polyurea.

Still alternatively, the method includes, for example, a method in which a second reaction solution, which is an aqueous solution comprising a water-soluble polymer and a water-soluble active hydrogen-containing compound, is added to a first reaction solution comprising pyroxasulfone in the crystalline state, a hydrophobic polyisocyanate and a non-volatile hydrophobic solvent and subsequently the resulted mixture is stirred at a high speed and then heated so as to allow the hydrophobic polyisocyanate, the water-soluble polymer and the water-soluble active hydrogen-containing compound to react, thereby obtaining microcapsules in which pyroxasulfone has been enclosed in the wall member made of polyurethane or polyurea.

In the above-described methods, it is optional that the process in which pyroxasulfone in the crystalline state may be blended in a first reaction solution may be replaced by mixing a first reaction solution comprising a hydrophobic polyisocyanate and a non-volatile hydrophobic solvent and a second reaction solution, which is an aqueous solution comprising a water-soluble polymer and a water-soluble active hydrogen-containing compound and then adding pyroxasulfone to the resultant mixed solution with stirring at a high speed.

In the respective methods described above, it is also optional that the first reactant solution and an aqueous solution of a water-soluble polymer may be mixed together and then the active hydrogen-containing compound to be contained in the second reactant solution may be added thereto to effect the reaction under gentle stirring.

In this case, the hydrophobic polyisocyanate used in combination with pyroxasulfone in the first reactant solution includes, for example, a dimmer or trimer of an aliphatic or aromatic diisocyanate or a polymethylene polyphenyl polyisocyanate expressed by the following formula (I)

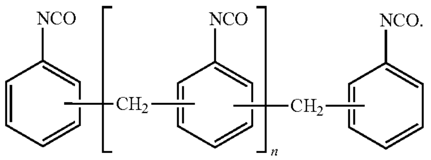

(I)

In the first reactant solution, the hydrophobic solvent for dissolving or suspending pyroxasulfone and the hydrophobic polyisocyanate is not particularly limited but, for example, includes ethers such as ethyl ether, dioxane, ethyleneglycol monoethyl ether, dipropyl ether, dibutyl ether, tetrahydrofuran and the like, aliphatic hydrocarbons such as normal paraffins, naphthenes, isoparaffins, kerosene, mineral oils and the like, aromatic hydrocarbons such as benzene, toluene, xylene, solvent naphtha, alkyl naphthalenes, phenyl xylyl ethane and the like, halogenated hydrocarbons such as dichloromethane, chloroform, carbon tetrachloride and the like, esters such as ethyl acetate, diisopropyl phthalate, dibutyl phthalate, dioctyl phthalate, dimethyl adipate, diisobutyl adipate, diisodecyl adipate, and the like, vegetable oils such as soybean oil, rapeseed oil, cottonseed oil, castor oil and the like and so on, of which phenyl xylyl ethane is particularly preferred.

Next, the water-soluble polymer used as the constituent of the second reactant solution is not particularly limited but, for example, includes polyacrylic acid and water-soluble salts thereof, polyethyleneglycols, poly(vinylpyrrolidone), poly(vinyl alcohol) and the like. A concentration of the water-soluble polymer in the aqueous solution is not particularly limited but usually selected in the range of 0.5 to 5% by mass.

Further, as the water-soluble active hydrogen-containing compound to be contained in the above-described second reactant solution, for example, hydroxyl compounds such as glycols, glycerol and the like and amino compounds such as ethylenediamine and the like are used. Water can also play a role as the active hydrogen-containing compound but need not be added separately because of the presence as the medium in the aqueous solutions.

The reaction between the first reactant solution and the second reactant solution proceeds by, for example, mixing them with high-speed stirring at a velocity of 1000 to 10000 rpm and then stirring the same for about 10 minutes to 6 hours at a room temperature or at a temperature of 50 to 100° C. under heating, although the condition depends on the hydrophobic polyisocyanete, hydrophobic solvent and water-soluble polymer to be selected.

By the above-described reaction, a polyurethane or polyurea is formed to serve as the wall member of microcapsule when the active hydrogen-containing compound used is a hydroxyl compound or an amino compound or when water acts as the active hydrogen-containing compound, respectively. Accordingly, the use proportion of the hydrophobic polyisocyanate in the first reactant solution and the water-soluble active hydrogen-containing compound and the water-soluble polymer in the second reactant solution each as the reactant should be selected in accordance with the stoichiometric amounts based on the reaction equations for the formation of a polyurethane or polyurea, respectively.

The above-described reaction may be performed according to need in the presence of, for example, a water-soluble thickener such as xanthan gum, carboxymethylcellulose or a salt thereof, gum arabic, gelatin, dextrin and water-soluble starch, a nonionic surfactant such as sorbitan fatty acid esters, sucrose fatty acid esters, polyoxyethylene fatty acid esters, polyoxyethylene resinate esters, polyoxyethylene alkyl ethers, polyoxyethylene alkylphenyl ethers, polyoxyethylene-polyoxypropylene block copolymers, alkyl polyoxyethylene-polypropylene block copolymer ethers, polyoxyalkylene styrylphenyl ethers, polyoxyethylene castor oils, hydrogenated polyoxyethylene castor oils and the like, an anionic surfactant such as alkyl sulfate salts, alkylbenzene sulfonate salts, lignin sulfonate salts, alkyl sulfosuccinate salts, naphthalene sulfonate salts, alkylnaphthalene sulfonate salts, salts of naphthalenesulfonic acid-formalin condensate, salts of alkylnaphthalene sulfonic acid-formalin condensate and the like or an antifoaming agent such as polyalkylsiloxane, salts of higher fatty acid and the like. These additives may be added to the first reactant solution or to the second reactant solution in advance or alternatively may be added separately from the first reactant solution and second reactant solution.

As to the thus obtained masking material of the present invention which pyroxasulfone is microencapsulated in or coated with, an average particle size thereof (volume median diameter) can be freely selected. The said particle size is usually selected in the range of 0.1-150 μm, preferably, 0.5-100 μm, or more preferably, 1-50 μm.

According to need, the agrochemical composition for foliage treatment in the present invention may arbitrarily contain additional components usually used in agrochemical formulations.

The above-described additional components include, for example, carriers such as solid carriers, liquid carriers and the like, surfactants, binders, tackifiers, thickeners, colorants, spreaders, stickers, antifreezing agents, anticaking agents, disintegrators, stabilizers, antifoaming agents and the like. In addition thereto, according to need, preservatives, plant detritus and the like may be used as the additional component. These additional components may be used singly or may be used as a combination of two kinds or more.

The solid carrier includes, for example, natural minerals such as quartz, clay, quartz sand, kaolinite, pyrophyllite, sericite, talc, bentonite, acid clay, attapulgite, zeolite, diatomaceous earth and the like; inorganic salts such as calcium carbonate, ammonium sulfate, sodium sulfate, potassium chloride and the like; organic solid carriers such as synthetic silicic acid, synthetic silicate, starch, cellulose, vegetable powders and the like; plastic carriers such as polyethylene, polypropylene, poly(vinylidene chloride) and the like; urea, hollow inorganic bodies, hollow plastic bodies, fumed silica (white carbon) and the like. These may be used singly or may be used as a combination of two kinds or more.

The liquid carrier includes, for example, alcohols including monohydric alcohols such as methanol, ethanol, propanol, isopropanol, butanol and the like and polyhydric alcohols such as ethylene glycol, diethylene glycol, propylene glycol, hexylene glycol, poly(ethylene glycol), poly(propylene glycol), glycerol and the like; polyhydric alcohol compounds such as propylene glycol ether and the like; ketones such as acetone, methyl ethyl ketone, methyl isobutyl ketone, diisobutyl ketone, cyclohexanone and the like; ethers such as ethyl ether, dioxane, ethyleneglycol monoethyl ether, dipropyl ether, tetrahydrofuran and the like; aliphatic hydrocarbons such as normal paraffins, naphthenes, isoparaffins, kerosenes, mineral oils and the like; aromatic hydrocarbons such as benzene, toluene, xylene, solvent naphtha, alkylbenzenes, alkylnaphthalenes and the like; halogenated hydrocarbons such as dichloromethane, chloroform, carbon tetrachloride and the like; esters such as ethyl acetate, diisopropyl phthalate, dibutyl phthalate, dioctyl phthalate, dimethyl adipate and the like; lactones such as γ-butyrolactone and the like; amides such as dimethylformamide, diethylformamide, dimethylacetamide, N-alkylpyrrolidinone and the like; nitriles such as acetonitrile and the like; sulfur compounds such as dimethyl sulfoxide and the like; vegetable oils such as soybean oil, rapeseed oil, cottonseed oil, castor oil and the like; water; and so on. These may be used singly or may be used as a combination of two kinds or more.

The surfactant includes, for example, nonionic surfactants such as sorbitan fatty acid esters, polyoxyethylene sorbitan fatty acid esters, sucrose fatty acid esters, polyoxyethylene fatty acid esters, polyoxyethylene resinate esters, polyoxyethylene fatty acid diesters, polyoxyethylene alkyl ethers, polyoxyethylene alkylphenyl ethers, polyoxyethylene dialkyl phenyl ethers, polyoxyethylene alkyl phenyl ether-formalin condensates, polyoxyethylene-polyoxypropylene block copolymers, alkyl polyoxyethylene-polypropylene block copolymer ethers, polyoxyethylenealkylamines, polyoxyethylene fatty acid amides, polyoxyethylene fatty acid bisphenyl ethers, polyalkylene benzyl phenyl ethers, polyoxyalkylene styrylphenyl ethers, acetylene diols, polyoxyalkylene-added acetylene diols, polyoxyethylene ether-type silicones, ester-type silicones, fluorine surfactants, polyoxyethylene castor oils, hydrogenated polyoxyethylene castor oils and the like; anionic surfactants such as alkyl sulfate salts, polyoxyethylene alkyl ether sulfate salts, polyoxyethylene alkyl phenyl ether sulfate salts, polyoxyethylene styryl phenyl ether sulfate salts, alkylbenzenesulfonate salts, lignin sulfonate salts, alkylsulfosuccinate salts, naphthalenesulfonate salts, alkylnaphthalene sulfonate salts, salts of formalin condensate of naphthalene sulfonic acid, salts of formalin condensate of alkylnaphthalene sulfonic acid, fatty acid salts, polycarboxylate salts, N-methyl-fatty acid sarcosinate, resinates, polyoxyethylene alkyl ether phosphate salts, polyoxyethylene alkyl phenyl ether phosphate salts and the like; cationic surfactants such as laurylamine hydrochloride salts, stearylamine hydrochloride salts, oleylamine hydrochloride salts, stearylamine acetate salts, stearylaminopropylamine acetate salts, alkylamine salts including alkyltrimethylammonium chloride, alkyldimethylbenzalkonium chloride and the like, and so on; ampholytic surfactants such as amino acid or betaine surfactants and the like, and so on. These surfactants may be used singly or may be used as a combination of two kinds or more.

The binder and tackifier include, for example, carboxymethylcellulose and salts thereof, dextrin, water-soluble starch, xanthan gum, guar gum, sucrose, poly(vinylpyrrolidone), gum arabic, poly(vinyl alcohol), poly(vinyl acetate), sodium polyacrylate, polyoxyethylene with an average molecular weight of 6000 to 5000000, phospholipid (for example, cephalin, lecithin and the like) and so on. These binders and tackifiers may be used singly or may be used as a combination of two kinds or more.

The thickener includes, for example, water-soluble polymers such as xanthan gum, guar gum, carboxymethylcellulose, poly(vinylpyrrolidone), carboxyvinyl polymers, acrylic polymers, starch derivatives and polysaccharides; inorganic fine powders such as high-purity bentonite and fumed silica (white carbon), and the like. These thickeners may be used singly or may be used as a combination of two kinds or more.

The colorant includes, for example, inorganic pigments such as iron oxide, titanium oxide, and Prussian blue; organic dyes such as alizarin dye, azo dye, and metal phthalocyanine dye, and the like. These colorants may be used singly or may be used as a combination of two kinds or more.

The spreader includes, for example, cellulose powder, dextrin, modified starch, polyaminocarboxylic acid chelates compounds, crosslinked poly(vinylpyrrolidone), copolymers of maleic acid with a styrene compound, (meth)acrylic acid copolymers, half esters of a polymer consisting of polyhydric alcohol with dicarboxylic anhydride, water-soluble salts of polystyrenesulfonic acid and the like. These spreaders may be used singly or may be used as a combination of two kinds or more.

The sticker includes, for example, paraffin, terpene, polyamide resins, polyacrylate, polyoxyethylene, wax, polyvinyl alkyl ether, alkylphenol-formalin condensates, starch phosphate, synthetic resin emulsions and the like. These stickers may be used singly or may be used as a combination of two kinds or more.

The antifreezing agent includes, for example, polyhydric alcohols such as ethylene glycol, diethylene glycol, propylene glycol, glycerol and the like, and so on. These antifreezing agents may be used singly or may be used as a combination of two kinds or more.

The anticaking agent includes, for example, polysaccharides such as starch, alginic acid, mannose, galactose and the like; poly(vinylpyrrolidone), fumed silica (white carbon), ester gum, petroleum resins and the like. These anticaking agents may be used singly or may be used as a combination of two kinds or more.

The disintegrator includes, for example, sodium tripolyphosphate, sodium hexametaphosphate, metal stearates, cellulose powder, dextrin, methacrylate copolymers, poly(vinylpyrrolidone), polyaminocarboxylic acid chelate compounds, sulfonated styrene-isobutylene-maleic anhydride copolymers, starch-polyacrylonitrile graft copolymers and the like. These disintegrators may be used singly or may be used as a combination of two kinds or more.

The stabilizer includes, for example, desiccants such as zeolite, calcined lime and magnesium oxide; antioxidants such as phenol compounds, amine compounds, sulfur compounds, phosphoric acid compounds and the like; ultraviolet absorbers such as salicylic acid compounds, benzophenone compounds and the like; and so on. These stabilizers may be used singly or may be used as a combination of two kinds or more.

The antifoaming agent includes, for example, dimethylpolysiloxane, modified silicones, polyethers, fatty acid esters, fatty acid salts and the like. These antifoaming agents may be used singly or may be used as a combination of two kinds or more.

The preservative includes, for example, sodium benzoate, sodium p-hydroxybenzoate, potassium sorbate, 1,2-benzothiazolin-3-one and the like. These preservatives may be used singly or may be used as a combination of two kinds or more.

The plant detritus includes, for example, sawdust, coconut shell, corn cob, tobacco stalk and the like. The plant detritus may be used singly or may be used as a combination of two kinds or more.

When the above-mentioned additional components are contained in the inventive agrochemical composition for foliage treatment, a content thereof is selected in the range of, on a mass basis, usually 5 to 95% or, preferably, 20 to 90% as a carrier, usually 0.1 to 30% or, preferably, 0.5 to 10% as a surfactant, and, usually, 0.1 to 30% or, preferably, 0.5 to 10% as other additives.

As the agrochemical composition for foliage treatment in the present invention, a composition of a masking material which pyroxasulfone is microencapsulated in or coated with may be employed as it is. However, the inventive composition is usually employed with the above described additional components as formulated in any desired dosage forms including wettable powders, dust powders, water-dispersible granules, aqueous suspension concentrates, oil-based suspension concentrates, granules, jumbo formulations, suspo-emulsions and uniformly diffusible formulations. Among them, the favorite dosage forms include dust powders, granules, wettable powders, water-dispersible granules, aqueous suspension concentrates and oil-based suspension concentrates.

When the agrochemical composition for foliage treatment in the present invention is in the form of granules, examples of granules include spherical, columnar, spindle-shaped and irregular ones and other forms having a particle size of from 0.3 to 10 mm.

The spherical granule has a particle size of, usually, from 0.3 to 10 mm or, preferably, from 0.3 to 3 mm.

The columnar granule has a diameter of, usually, from 0.6 to 5 mm or, preferably, from 0.8 to 3 mm and a length of, usually, from 1 to 10 mm or, preferably, from 1.5 to 8 mm.

The spindle-shaped granule has a breadth of, usually, from 0.3 to 3 mm and a length of, usually, from 1 to 10 mm.

When the agrochemical composition for foliage treatment in the present invention is a uniformly diffusible formulation, it is preferable that the composition has a particle size distribution wherein at least 80% by mass of the granules have a particle size of 3 mm or larger and that, when the composition is put into water, the formulation floats on the water surface but the granules are disintegrated on the water surface within 30 minutes after putting.

In formulating the inventive agrochemical composition for foliage treatment, one, two or more other agrochemical active ingredients may be arbitrarily blended in addition to pyroxasulfone contained in the composition. The other agrochemical active ingredient as described herein may be blended in the inventive agrochemical composition by being enclosed or included in or coated with a masking material together with pyroxasulfone or the other agrochemical active ingredient, separately from pyroxasulfone, may be blended by being enclosed or included in or coated with a masking material in accordance with the description relating to the composition of the present invention. Alternatively, an arbitrary agrochemical active ingredient, which does not have a masking structure as used in the present invention, may be blended such that the effect of the present invention is not impaired. The term "arbitrary agrochemical active ingredient" includes pyroxasulfone. Further, any safener ingredients and agricultural materials including fertilizers and the like but excluding agrochemicals may be also blended to produce a mixed composition.

For the agrochemically active ingredients which may be blended in the present invention, examples of usable herbicidal active ingredients, insecticidally active ingredients, fungicidally active ingredients and plant growth regulating active ingredients will be described below but, the scope of the present invention is not limited to these agrochemical active ingredients.

Herbicidal Active Ingredient:

ioxynil, aclonifen, acrolein, azafenidin, acifluorfen (including its salts with sodium, e.g.), azimsulfuron, asulam, acetochlor, atrazine, anilofos, amicarbazone, amidosulfuron, amitrole, aminocyclopyrachlor, aminopyralid, amiprofos-methyl, ametryn, alachlor, alloxydim, isouron, isoxachlortole, isoxaflutole, isoxaben, isoproturon, ipfencarbazone, imazaquin, imazapic (including its salts with amines, e.g.), imazapyr (including its isopropylamine salt, e.g.), imazamethabenz-methyl, imazamox, imazethapyr, imazosulfuron, indaziflam, indanofan, eglinazine-ethyl, esprocarb, ethametsulfuron-methyl, ethalfluralin, ethidimuron, ethoxysulfuron, ethoxyfen-ethyl, ethofumesate, etobenzanid, endothal-disodium, oxadiazon, oxadiargyl, oxaziclomefone, oxyfluorfen, oryzalin, orthosulfamuron, orbencarb, cafenstrole, carfentrazone-ethyl, karbutilate, carbetamide, quizalofop (quizalofop-ethyl), quizalofop-P-ethyl, quizalofop-P-tefuryl, quinoclamine, quinclorac, quinmerac, cumyluron, clacyfos, glyphosate (including its sodium, potassium, amine, propylamine, isopropylamine, dimethylamine or trimesium salt, e.g.), glufosinate (including its amine or sodium salt, e.g.), clethodim, clodinafop-propargyl, clopyralid, clomazone, chlomethoxyfen, clomeprop, cloransulam-methyl, chloramben, chloridazon, chlorimuron-ethyl, chlorsulfuron, chlorthal-dimethyl, chlorthiamid, chlorphthalim, chlorflurenol-methyl, chlorpropham, chlorbromuron, chloroxuron, chlorotoluron, saflufenacil, cyanazine, cyanamide, diuron, diethatyl-ethyl, dicamba (including its amine, diethylamine, isopropylamine, diglycolamine, sodium or lithium salt, e.g.), cycloate, cycloxydim, diclosulam, cyclosulfamuron, cyclopyrimorate, dichlobenil, diclofop-P-methyl, diclofop-methyl, dichlorprop, dichlorprop-P, diquat, dithiopyr, siduron, dinitramine, cinidon-ethyl, cinosulfuron, dinoterb, cyhalofop-butyl, diphenamid, difenzoquat, diflufenican, diflufenzopyr, simazine, dimethachlor, dimethametryn, dimethenamid, dimethenamid-P, simetryn, dimepiperate, dimefuron, cinmethylin, swep, sulcotrione, sulfentrazone, sethoxydim, terbacil, daimuron, dalapon, thiazopyr, tiafenacil, thiencarbazone (including its sodium salt or methyl ester, e.g.), tiocarbazil, thiobencarb, thidiazimin, thifensulfuron-methyl, desmedipham, desmetryne, thenylchlor, tebutam, tebuthiuron, tepraloxydim, tefuryltrione, tembotrione, terbuthylazine, terbutryn, terbumeton, topramezone, tralkoxydim, triaziflam, triasulfuron, triafamone, tri-allate, trietazine, triclopyr, triclopyr-butotyl, trifludim oxazin, tritosulfuron, triflusulfuron-methyl, trifluralin, trifloxysulfuron-sodium, tribenuron-methyl, tolpyralate, naptalam (including its salts with sodium, e.g.), naproanilide, napropamide, napropamide-M, neburon, norflurazon, vernolate, paraquat, halauxifen-methyl, haloxyfop, haloxyfop-P, haloxyfop-etotyl, halosulfuron-methyl, picloram, picolinafen, bicyclopyrone, bispyribac-sodium, pinoxaden, bifenox, piperophos, pyraclonil, pyrasulfotole, pyrazoxyfen, pyrazolynate, bilanafos, pyraflufen-ethyl, pyridafol, pyrithiobac-sodium, pyridate, pyriftalid, pyributicarb, pyribenzoxim, pyrimisulfan, pyriminobac-methyl, pyroxsulam, phenisopham, fenuron, fenoxasulfone, fenoxaprop-P-ethyl, fenquinotrione, fenthiaprop-ethyl, fentrazamide, phenmedipham, foramsulfuron, butachlor, butafenacil, butamifos, butylate, butenachlor, butralin, butroxydim, flazasulfuron, flamprop (including its methyl, ethyl or isopropyl ester), flamprop-M (including its methyl, ethyl or isopropyl ester), fluazifop-butyl, fluazifop-P-butyl, fluazolate, fluometuron, fluoroglycofen-ethyl, flucarbazone-sodium, fluchloralin, flucetosulfuron, fluthiacet-methyl, flupyrsulfuron-methyl-sodium, flufenacet, flufenpyr-ethyl, flupropanate, flupoxame, flumioxazin, flumiclorac-pentyl, flumetsulam, fluridone, flurtamone, fluroxypyr, flurochloridone, pretilachlor, procarbazone-sodium, prodiamine, prosulfocarb, propaquizafop, propachlor, propazine, propanil, propyzamide, propisochlor, propyrisulfuron, propham, profluazol, propoxycarbazone-sodium, profoxydim, bromacil, brompyrazon, prometryn, prometon, bromoxynil (including its ester body of butyric acid, octane acid or heptane acid, e.g.), bromofenoxim, bromobutide, florasulam, pethoxamid, benazolin, penoxsulam, heptamaloxyloglucan, beflubutamid, pebulate, bencarbazone, pendimethalin, benzfendizone, bensulide, bensulfuron-methyl, benzobicyclon, benzofenap, bentazone, pentanochlor, pentoxazone, benfluralin, benfuresate, fosamine, fomesafen, mecoprop (including its sodium, potassium, isopropylamine, triethanolamine or dimethylamine salt, e.g.), mecoprop-P-pottasium, mesosulfuron-methyl, mesotrione, metazachlor, metazosulfuron, methabenzthiazuron, metamitron, metamifop, methiozolin, methyldymuron, metoxuron, metosulam, metobromuron, metobenzuron, metolachlor, metribuzin, mefenacet, monolinuron, molinate, iodosulfuron, iodosulfulon-methyl-sodium, iofensulfuron, iofensulfuron-sodium, lactofen, linuron, lenacil, 2,3,6-TBA (2,3,6-trichloro benzoic acid), 2,4,5-T [(2,4,5-trichlorophenoxy)acetic acid], 2,4-D [(2,4-dichlorophenoxy)acetic acid] (including its amine, diethylamine, triethanolamine, isopropylamine, sodium or lithium salt, e.g.), 2,4-DB [4-(2,4-dichlorophenoxy)butyric acid], AE-F-150944 (Code No.), DNOC (4,6-dinitro-o-cresol) (including its amine or sodium salt, e.g.), EPTC [S-ethyl dipropyl(thiocarbamate)], MCPA (2-methyl-4-chlorophenoxyacetic acid), MCPA-thioethyl, MCPB [(2-methyl-4-chlorophenoxy)butyric acid] (including its sodium salt or ethyl ester, e.g.), SYP-298 (Code No.), SYP-300 (Code No.), S-metolachlor, and TCA (2,2,2-trichloroacetic acid) (including its sodium, calcium or ammonia salt, e.g.).

Insecticidally Active Ingredients:

acrinathrin, azadirachtin, azamethiphos, azinphos-ethyl, azinphos-methyl, acequinocyl, acetamiprid, acetoprole, acephate, azocyclotin, abamectin, afidopyropen, amidoflumet, amitraz, alanycarb, aldicarb, aldoxycarb, allethrin (including its d-cis-trans body and d-trans body), isazophos, isamidofos, isocarbophos, isoxathion, isofenphos-methyl, isoprocarb, ivermectin, imicyafos, imidacloprid, imiprothrin, indoxacarb, esfenvalerate, ethiofencarb, ethion, ethiprole, ethylene dibromide, etoxazole, etofenprox, ethoprophos, etrimfos, emamectin benzoate, endosulfan, empenthrin, oxamyl, oxydemeton-methyl, oxydeprofos, omethoate, cadusafos, kappa-tefluthrin, kappa-bifenthrin, karanjin, cartap, carbaryl, carbosulfan, carbofuran, gamma-BHC, xylylcarb, quinalphos, kinoprene, chinomethionat, coumaphos, cryolite, clothianidin, clofentezine, chromafenozide, chlorantraniliprole, chlorethoxyfos, chlordane, chloropicrin, chlorpyrifos, chlorpyrifos-methyl, chlorfenapyr, chlorfenvinphos, chlorfluazuron, chlormephos, cyanophos, diafenthiuron, diamidafos, cyantraniliprole, dienochlor, cyenopyrafen, dioxabenzofos, diofenolan, cyclaniliprole, dicrotophos, dichlofenthion, cycloprothrin, dichlorvos, dicloromezotiaz, 1,3-dichloropropene, dicofol, dicyclanil, disulfoton, dinotefuran, dinobuton, cyhalothrin (including its gamma-body and lambda-body), cyphenothrin (including its (1R)-trans-body), cyfluthrin (including its beta-body), diflubenzuron, cyflumetofen, diflovidazin, cyhexatin, cypermethrin (including its alpha-body, beta-body, theta-body, and zata-body), dimethylvinphos, dimefluthrin, dimethoate, silafluofen, cyromazine, spinetoram, spinosad, spirodiclofen, spirotetramat, spiromesifen, sulcofuron-sodium, sulfluramid, sulfoxaflor, sulfotep, diazinon, thiacloprid, thiamethoxam, tioxazafen, thiodicarb, thiocyclam, thiosultap, thionazin, thiofanox, thiometon, tetrachlorvinphos, tetradifon, tetraniliprole, tetramethylfluthrin, tetramethrin, tebupirimfos, tebufenozide, tebufenpyrad, tefluthrin, teflubenzuron, demeton-S-methyl, temephos, deltamethrin, terbufos, tralomethrin, transfluthrin, triazamate, triazophos, trichlorfon, triflumuron, triflumezopyrim, trimethacarb, tolfenpyrad, naled, nitenpyram, novaluron, noviflumuron, *Verticillium lecanii,* hydroprene, spore of *Pasteuriapenetrans,* vamidothion, parathion, parathion-methyl, halfenprox, halofenozide, bioallethrin, bioallethrin S-cyclopentenyl, bioresmethrin, bistrifluron, hydramethylnon, bifenazate, bifenthrin, pyflubumide, piperonyl butoxide, pymetrozine, pyraclofos, pyrafluprole, pyridaphenthion, pyridaben, pyridalyl, pyrifluquinazon, pyriprole, pyriproxyfen, pirimicarb, pyrimidifen, pyriminostrobin, pirimiphos-methyl, pyrethrine, famphur, fipronil, fenazaquin, fenamiphos, fenitrothion, fenoxycarb, fenothiocarb, phenothrin (including its (1R)-trans-body), fenobucarb, fenthion, phenthoate, fenvalerate, fenpyroximate, fenbutatin oxide, fenpropathrin, fonofos, sulfuryl fluoride, butocarboxim, butoxycarboxim, buprofezin, furathiocarb, prallethrin, fluacrypyrim, fluazuron, fluensulfone, sodium fluoroacetate, flucycloxuron, flucythrinate, flusulfamide, fluvalinate (including its tau-body), flupyradifurone, flupyrazofos, flufiprole, flufenerim, flufenoxystrobin, flufenoxuron, fluhexafon, flubendiamide, flumethrin, prothiofos, protrifenbute, flonicamid, propaphos, propargite, profenofos, broflanilide, profluthrin, propetamphos, propoxur, flometoquin, bromopropylate, hexythiazox, hexaflumuron, *Paecilomyces tenuipes, Paecilomyces fumosoroceus,* heptafluthrin, heptenophos, permethrin, benclothiaz, bensultap, benzoximate, bendiocarb, benfuracarb, *Beauveria tenella, Beauveria bassiana, Beauveria brongniartii,* phoxim, phosalone, fosthiazate, fosthietan, phosphamidon, phosmet, polynactins, formetanate, phorate, malathion, milbemectin, mecarbam, mesulfenfos, methoprene, methomyl, metaflumizone, methamidophos, metham, methiocarb, methidathion, methyl isothiocyanate, methyl bromide, methoxychlor, methoxyfenozide, methothrin, metofluthrin, methoprene, metolcarb, mevinphos, meperfluthrin, Monacrosporium phymatophagum, monocrotophos, momfluorothrin, litlure-A, litlure-B, aluminium phosphide, zinc phosphide, phosphine, lufenuron, rescalure, resmethrin, lepimectin, rotenone, fenbutatin oxide, calcium cyanide, nicotinesulfate, (Z)-11-tetradecenyl acetate, (Z)-11-hexadecenal, (Z)-11-hexadecenyl acetate, (Z)-9,12-tetradecadienyl acetate, (Z)-9-tetradecen-1-ol, (Z,E)-9,11-tetradecadienyl acetate, (Z,E)-9,12-tetradecadienyl acetate, *Bacillus popilliae, Bacillus subtillis, Bacillus sphaericus, Bacillus thuringiensis* subsp. *Aizawai, Bacillus thuringiensis* subsp. *Israelensis, Bacillus thuringiensis* subsp. *Kurstaki, Bacillus thuringiensis* subsp. *Tenebrionis,* Bt proteins (Cryl Ab, CrylAc, CrylFa, Cry2Ab, mCry3A, Cry3Ab, Cry3Bb, Cry34/35Ab1), CL900167 (Code No.), DCIP (bis-(2-chloro-1-methylethyl)ether), DDT (1,1,1-trichloro-2,2-bis (4-chlorophenyl)ethane), DEP (dimethyl-2,2,2-trichloro-1-hydroxyethylphosphonate), DNOC (4,6,-dinitro-o-cresol), DSP (O,O-diethyl-O-[4-dimethylsulfamoyl]phenyl) phosphorothioate), EPN (O-ethyl O-(4-nitrophenyl) phenylphosphonothioate), NA-85 (Code No.), NA-89 (Code No.), NC-515 (Code No.), RU15525 (Code No.), ZDI-2501 (Code No.), XMC, Z-13-eicosene-10-one, ZXI8901 (Code No.), and ME5382.

Fungicidally Active Ingredient:

azaconazole, acibenzolar-S-methyl, azoxystrobin, anilazine, amisulbrom, ametoctradin, aldimorph, isotianil, isopyrazam, isofetamid, isoprothiolane, ipconazole, iprodione, iprovalicarb, iprobenfos, imazalil, iminoctadine-trialbesilate, iminoctadine-triacetate, imibenconazole, edifenphos, etaconazole, ethaboxam, ethirimol, ethoxyquin, etridiazole, enestroburin, enoxastrobin, epoxiconazole, organic oils, oxadixyl, oxazinylazole, oxathiapiprolin, oxycarboxin, oxine-copper, oxytetracycline, oxpoconazole-fumarate, oxolinic acid, copper dioctanoate, octhilinone, ofurace, orysastrobin, o-phenylphenol, kasugamycin, captafol, carpropamid, carbendazim, carboxin, carvone, quinoxyfen, chinomethionat, captan, quinconazole, quintozene, guazatine, cufraneb, coumoxystrobin, kresoxim-methyl, clozylacon, chlozolinate, chlorothalonil, chloroneb, cyazofamid, diethofencarb, diclocymet, dichlofluanid, diclomezine, dicloran, dichlorophen, dithianon, diniconazole, diniconazole-M, zineb, dinocap, dipymetitrone, diphenylamine, difenoconazole, cyflufenamid, diflumetorim, cyproconazole, cyprodinil, simeconazole, dimethirimol, dimethyl disulfide, dimethomorph, cymoxanil, dimoxystrobin, ziram, silthiofam, streptomycin, spiroxamine, sedaxane, zoxamide, dazomet, tiadinil, thiabendazole, thiram, thiophanate, thiophanate-methyl, thifluzamide, tecnazene, tecloftalam, tetraconazole, debacarb, tebuconazole, tebufloquin, terbinafine, dodine, dodemorph, triadimenol, triadimefon, triazoxide, trichlamide, triclopyricarb, tricyclazole, triticonazole, tridemorph, triflumizole, trifloxystrobin, triforine, tolylfluanid, tolclofos-methyl, tolnifanide, tolprocarb, nabam, natamycin, naftifine, nitrapyrin, nitrothal-isopropyl, nuarimol, copper nonyl phenol sulphonate, *Bacillus subtilis* (strain: QST 713), validamycin, valifenalate, picarbutrazox, bixafen, picoxystrobin, bitertanol, binapacryl, biphenyl, piperalin, hymexazol, pyraoxystrobin, pyraclostrobin, pyraziflumid, pyrazophos, pyrametostrobin, pyriofenone, pyrisoxazole, pyrifenox, pyributicarb, pyribencarb, pyrimethanil, pyroquilon, vinclozolin, ferbam, famoxadone, phenazine oxide, fenamidone, fenaminstrobin, fenarimol, fenoxanil, ferimzone, fenpiclonil, fenpyrazamine, fenbuconazole, fenfuram, fenpropidin, fenpropimorph, fenhexamid, folpet, phthalide, bupirimate, fuberidazole, blasticidin-S, furametpyr, furalaxyl, furancarboxylic acid, fluazinam, fluoxastrobin, fluopicolide, fluopyram, fluoroimide, fluxapyroxad, fluquinconazole, furconazole, furconazole-cis, fludioxonil, flusilazole, flusulfamide, flutianil, flutolanil, flutriafol, flufenoxystrobin, flumetover, flumorph, proquinazid, prochloraz, procymidone, prothiocarb, prothioconazole, bronopol, propamocarb-hydrochloride, propiconazole, propineb, probenazole, bromuconazole, hexaconazole, benalaxyl, benalaxyl-M, benodanil, benomyl, pefurazoate, penconazole, pencycuron, benzovindiflupyr, benthiazole, benthiavalicarb-isopropyl, penthiopyrad, penflufen, boscalid, fosetyl (alminium, calcium, sodium), polyoxin, polycarbamate, Bordeaux mixture, mancozeb, mandipropamid, mandestrobin, maneb, myclobutanil, mineral oils, mildiomycin, methasulfocarb, metam, metalaxyl, metalaxyl-M, metiram, metconazole, metominostrobin, metrafenone, mepanipyrim, meptyldinocap, mepronil, iodocarb, laminarin, phosphorous acid and its salts, copper oxychloride, silver, cuprous oxide, copper hydroxide, potassium bicarbonate, sodium bicarbonate, sulfur, oxyquinoline sulfate, copper sulfate, (3,4-dichloroisothiazol-5-yl) methyl-4-(tert-butyl)benzoate (IUPAC Name, CAS No. 1231214-23-5), 3-((3,4-dichloroisothiazole-5-yl)methoxy)benzo[d]isothiazole-1,1-dioxide (IUPAC Name, CAS No. 957144-77-3), BAF-045 (Code No.), BAG-010 (Code No.), DBEDC (Dodecylbenzenesulphonic acid bisethylenediamine copper [II] salt), MIF-1002 (Code No.), TPTA (fentin-acetate), TPTC (triphenyltin chloride), and TPTH (fentin hydroxide).

Plant Growth Regulating Active Ingredients:

1-naphthyl acetamide, 1-methylcyclopropene,2, 6-diisopropylnaphthalene, 4-CPA (4-chlorophenoxy) acetic acid), 4-oxo-4-(2-phenylethyl) aminobutyric acid (IUPAC Name, CAS No. 1083-55-2), aviglycine, ancymidol, inabenfide, indole acetic acid, indole butyric acid, uniconazole, uniconazole-P, ethychlozate, ethephon, epocholeone, carvone, cloxyfonac, cloxyfonac-potassium, cloprop, chlormequat, cytokinins, cyclanilide, dikegulac, gibberellins, dimethipin, sintofen, daminozide, thidiazuron, n-decyl alcohol (n-decanol), triacontanol, trinexapac-ethyl, paclobutrazol, flumetralin, flurprimidol, flurenol, prohydrojasmon, prohexadione-calcium, benzylaminopurine, forchlorfenuron, maleic hydrazide, mepiquat chloride, and mefluidide.

Examples of safener ingredients which may be blended in the present invention will be described below but, the scope of the present invention is not limited to these safener ingredients.

Safener Ingredients:

AD-67 (4-dichloroacetyl-1-oxa-4-azaspiro[4.5] decane), DKA-24 (N1, N2-diallyl-N2-dichloroacetylglycinamide), MG-191 (2-dichloromethyl-2-methyl-1,3-dioxane), MON4660 (Code No.), N-(2-methoxybenzoyl)-4-[(methylaminocarbonyl)amino] benzenesulfonamide (IUPAC Name, CAS No. 129531-12-0), PPG-1292 (2,2-dichloro-N-(1,3-dioxane-2-ylmethyl)-N-(2-propenyl) acetamide), R-29148 (3-dichloroacetyl-2,2,5-trimethyl-1,3-oxazolidine), TI-35 (Code No.), isoxadifen, isoxadifen-ethyl, oxabetrinil, cloquintcet-mexyl, cyometrinil, dichlormid, dicyclonone, cyprosulfamide, 1,8-Naphthalic Anhydride, fenchlorazole-ethyl, fenclorim, furilazole, fluxofenim, flurazole, benoxacor, mefenpyr, mefenpyr-ethyl, mefenpyr-diethyl, and lower alkyl-substituted benzoic acids.

The inventive agrochemical composition for foliage treatment which is formulated in any aforementioned dosage form may be wrapped with a water-soluble film so as, in this way, to contribute to labor saving in the application thereof along with an increase in the safety.

The preparation method of the inventive agrochemical composition for foliage treatment is not particularly limitative but usually includes the following methods:

(1) a method in which a blend of pyroxasulfone microencapsulated in or coated with a masking material and other starting materials is admixed with an appropriate volume of water for kneading followed by extrusion through a screen having an opening of a specified size for granulation and then drying;

(2) a method in which pyroxasulfone microencapsulated in or coated with a masking material and other starting materials are mixed with water or a suitable solvent to be uniformly suspended therein; and (3) a method in which pyroxasulfone microencapsulated in or coated with a masking material is blended with an appropriate carrier followed by drying and then blended with other starting materials.

Immediately after foliage treatment is performed with the inventive agrochemical composition for foliage treatment, pyroxasulfone is sufficiently masked but, with time, such a masking effect is quickly diminished. To confirm such a performance, an evaluation can be made by the following method. Namely, a concentration of pyroxasulfone in water, $K_1$, and another concentration of pyroxasulfone in water, $K_{24}$, are measured 1 hour and 24 hours after a pre-determined amount of the sample composition is added to water at 20° C., respectively. When $K_{24}$ is equal to or less than twice a solubility of pyroxasulfone in water and $K_1$ is sufficiently lower than $K_{24}$, the agrochemical composition for foliage treatment in the present invention exhibits a desired effect and thus the performance is confirmed to be preferable. In the inventive agrochemical composition for foliage treatment, $K_1$ is usually equal to or less than 55%, preferably, equal to or less than 50% or, more preferably, equal to or less than 45% of $K_{24}$.

The method of applying the above-described agrochemical composition for foliage treatment according to the present invention for foliage spraying over an upland field where a cultivated crop in the growing period thereof is growing is not particularly limited and may be performed depending on a dosage form of the composition in accordance with an ordinary method in the art. The cultivated crop includes *Triticum aestivum, Hordeum vulgare, Secale cereale, Zea mays, Sorghum bicolor, Glycine max, Brassica rapa, Carthamus tinctorius, Helianthus annuus, Linum usitatissimum, Arachis hypogaea, Sesamum indicum, Solanum tuberosum, Ipomoea batatas, Allium cepa, Allium sativum, Beta vulgaris,* cotton plants, mint plants, and lawn plants.

EXAMPLES

In the following, the present invention will be described in detail by way of Examples and Test Examples but, the present invention is not restricted by these Examples. In the following Examples, the "parts" and the "%" represents parts by mass and % by mass, respectively.

Example 1

A solution prepared by dissolving 1 part of pyroxasulfone and 2 parts of ethylcellulose into 100 parts of dichloromethane was added to 100 parts of a 1% aqueous polyvinyl alcohol solution and stirred for 10 minutes with a dissolver (manufactured by PRIMIX Corp., product name "T.K. ROBOMIX", the same applying hereafter) at a revolution of 6000 rpm. Thereafter, the mixed solution was gently stirred for 3 hours at 60° C. and dichloromethane was distilled off, thereby to obtain an agrochemical composition for foliage treatment containing the microencapsulated pyroxasulfone wherein the masking material is ethyl cellulose. This composition had spherical granules having an average particle size of 12 μm.

Example 2

A solution prepared by dissolving 1 part of pyroxasulfone and 2 parts of a polyester resin into 100 parts of dichloromethane was added to 100 parts of a 1% aqueous polyvinyl alcohol solution and stirred for 10 minutes with a dissolver at a revolution of 6000 rpm. Thereafter, the mixed solution was gently stirred for 3 hours at 60 ° C. and dichloromethane was distilled off, thereby to obtain an agrochemical composition for foliage treatment containing the microencapsulated pyroxasulfone wherein the masking material is polyester. This composition had spherical granules having an average particle size of 11 μm.

Example 3

1 Part of pyroxasulfone was added into a solution prepared by suspending 2.5 parts of a polymethylene polyphenyl polyisocyanate (produced by Tosoh Corp., product name "Millionate MR-100"), 10 parts of diisobutyl adipate (produced by Kao Corp., product name "Vinycizer-40") and 50 parts of a 1% aqueous polyvinyl alcohol solution and stirred for 3 minutes with a dissolver at a revolution of 2000 rpm. Thereafter, the mixed solution was gently stirred for 1 hour at 50° C., thereby to obtain an agrochemical composition for foliage treatment containing the microencapsulated pyroxasulfone wherein the masking material is polyurea. This composition had spherical granules having an average particle size of 20 μm.

Example 4

1 Part of pyroxasulfone was added into a solution prepared by suspending 2.5 parts of a polymethylene polyphenyl polyisocyanate (produced by Tosoh Corp., product name "Millionate MR-100"), 10 parts of an aromatic hydrocarbon solvent (produced by Exxon Mobil Corp., product name "Solvesso 200") and 50 parts of a 1% aqueous polyvinyl alcohol solution and stirred for 3 minutes with a dissolver at a revolution of 2000 rpm. Thereafter, the mixed solution was gently stirred for 1 hour at 50° C., thereby to obtain an agrochemical composition for foliage treatment containing the microencapsulated pyroxasulfone wherein the masking material is polyurea. This composition had spherical granules having an average particle size of 15 μm.

Example 5

A solution prepared by suspending and dissolving 2 parts of pyroxasulfone, 5 parts of a polymethylene polyphenyl polyisocyanate (produced by Tosoh Corp., product name "Millionate MR-100") into 6 parts of a machine oil was added to 50 parts of a 1% aqueous polyvinyl alcohol solution and stirred for 20 minutes with a dissolver at a revolution of 2000 rpm. Thereafter, the mixed solution was stirred at 1400 rpm for 1 hour at 60 ° C., thereby to obtain an agrochemical composition for foliage treatment containing the microencapsulated pyroxasulfone wherein the masking material is polyurea. This composition had spherical granules having an average particle size of 108 μm.

Example 6

A solution prepared by suspending and dissolving 2 parts of pyroxasulfone and 6 parts of a polymethylene polyphenyl polyisocyanate (produced by Tosoh Corp., product name "Millionate MR-100") to 6 parts of diisodecyl adipate (produced by Kao Corp., product name "Vinycizer-50") was added to 100 parts of a 1% aqueous polyvinyl alcohol solution and stirred for 10 minutes with a dissolver at a revolution of 3000 rpm. Thereafter, the mixed solution was stirred at 3000 rpm for 1 hour at 60° C. followed by allowing the mixed solution to cool to a room temperature, and 0.4 part of xanthan gum and 0.5 part of dimethylpolysiloxane were added thereto and stirred at 3000 rpm for 10 minutes, thereby to obtain an agrochemical composition for foliage treatment containing the microencapsulated pyroxasulfone wherein the masking material is polyurea. This composition had spherical granules having an average particle size of 22 μm.

Example 7

A solution prepared by suspending and dissolving 1 part of pyroxasulfone and 10 parts of a polymethylene polyphenyl polyisocyanate (produced by Tosoh Corp., product name "Millionate MR-100") to 15 parts of phenyl xylyl ethane (produced by JX Nippon Oil & Energy Corp., product name "Hisol SAS-296") was added to 100 parts of a 1% aqueous polyvinyl alcohol solution and stirred for 10 minutes with a dissolver at a revolution of 6000 rpm. Thereafter, 0.3 part of dimethylpolysiloxane was added to the mixed solution and gently stirred for 3 hours at 60° C., thereby to obtain an agrochemical composition for foliage treatment containing the microencapsulated pyroxasulfone wherein the masking material is polyurea. This composition had spherical granules having an average particle size of 5 μm.

Example 8

A solution prepared by suspending and dissolving 1 part of pyroxasulfone and 30 parts of a polymethylene polyphenyl polyisocyanate (produced by Tosoh Corp., product name "Millionate MR-100") to 15 parts of phenyl xylyl ethane (produced by JX Nippon Oil & Energy Corp., product name "Hisol SAS-296") was added to 100 parts of a 1% aqueous polyvinyl alcohol solution and stirred for 10 minutes with a dissolver at a revolution of 6000 rpm. Thereafter, 0.3 part of dimethylpolysiloxane was added to the mixed solution and gently stirred for 3 hours at 60° C., thereby to obtain an agrochemical composition for foliage treatment containing the microencapsulated pyroxasulfone wherein the masking material is polyurea. This composition had spherical granules having an average particle size of 18 μm.

Example 9

10 Parts of pyroxasulfone were added to a solution prepared by suspending and dissolving 8 parts of a polymethylene polyphenyl polyisocyanate (produced by Tosoh Corp., product name "Millionate MR-100"), 10 parts of phenyl xylyl ethane (produced by JX Nippon Oil & Energy Corp., product name "Hisol SAS-296") and 100 parts of a 1% aqueous polyvinyl alcohol solution and stirred for 10 minutes with a dissolver at a revolution of 6000 rpm. Thereafter, 3 parts of dimethylpolysiloxane were added to the mixed solution and gently stirred for 3 hours at 60° C., thereby to obtain an agrochemical composition for foliage treatment containing the microencapsulated pyroxasulfone wherein the masking material is polyurea. This composition had spherical granules having an average particle size of 8 μm.

Example 10

10 Parts of pyroxasulfone were added to a solution prepared by suspending 25 parts of a polymethylene polyphenyl polyisocyanate (produced by Tosoh Corp., product name "Millionate MR-100"), 10 parts of phenyl xylyl ethane (produced by JX Nippon Oil & Energy Corp., product name "Hisol SAS-296") and 155 parts of a 1% aqueous polyvinyl alcohol solution and stirred for 10 minutes with a dissolver at a revolution of 6000 rpm. Thereafter, 3 parts of dimethylpolysiloxane were added to the mixed solution and gently stirred for 3 hours at 60° C., thereby to obtain an agrochemical composition for foliage treatment containing the microencapsulated pyroxasulfone wherein the masking material is polyurea. This composition had spherical granules having an average particle size of 15 μm.

Example 11

10 Parts of pyroxasulfone were added to a solution prepared by suspending 40 parts of a polymethylene polyphenyl polyisocyanate (produced by Tosoh Corp., product name "Millionate MR-100"), 10 parts of phenyl xylyl ethane (produced by JX Nippon Oil & Energy Corp., product name "Hisol SAS-296") and 140 parts of a 1% aqueous polyvinyl alcohol solution and stirred for 10 minutes with a dissolver at a revolution of 6000 rpm. Thereafter, 3 parts of dimethylpolysiloxane were added to the mixed solution and gently stirred for 3 hours at 60° C., thereby to obtain an agrochemical composition for foliage treatment containing the microencapsulated pyroxasulfone wherein the masking material is polyurea. This composition had spherical granules having an average particle size of 28 μm.

Example 12

10 Parts of pyroxasulfone were added to a solution prepared by suspending 5 parts of a polymethylene polyphenyl polyisocyanate (produced by Tosoh Corp., product name "Millionate MR-100"), 10 parts of phenyl xylyl ethane (produced by JX Nippon Oil & Energy Corp., product name "Hisol SAS-296") and 75 parts of a 1% aqueous polyvinyl alcohol solution and stirred for 10 minutes with a dissolver at a revolution of 3000 rpm. Thereafter, 3 parts of dimethylpolysiloxane were added to the mixed solution and gently stirred for 3 hours at 60° C., thereby to obtain an agrochemical composition for foliage treatment containing the microencapsulated pyroxasulfone wherein the masking material is polyurea. This composition had spherical granules having an average particle size of 28 μm.

Example 13

An agrochemical composition for foliage treatment containing the microencapsulated pyroxasulfone wherein the masking material is polyurea was obtained in the same manner as in Example 12 except that a revolution of the dissolver was changed from 3000 rpm to 1000 rpm. This composition had spherical granules having an average particle size of 89 μm.

Example 14

10 Parts of pyroxasulfone were added to a solution prepared by suspending and dissolving 8 parts of 4,4'-diphenylmethane diisocyanate (produced by Tosoh Corp., product name "CORONATE 1130"), 10 parts of phenyl xylyl ethane (produced by JX Nippon Oil & Energy Corp., product name "Hisol SAS-296") and 100 parts of a 1% aqueous polyvinyl alcohol solution and stirred for 10 minutes with a dissolver at a revolution of 2500 rpm. Thereafter, 3 parts of dimethylpolysiloxane were added to the mixed solution and gently stirred for 3 hours at 60° C., thereby to obtain an agrochemical composition for foliage treatment containing the microencapsulated pyroxasulfone wherein the masking material is polyurea. This composition had spherical granules having an average particle size of 38 μm.

Example 15

10 Parts of pyroxasulfone were added to a solution prepared by suspending and dissolving 8 parts of a mixture of 4,4'-diphenylmethane diisocyanate and 2,6-tolylene diisocyanate (produced by Tosoh Corp., product name "CORONATE 1021"), 10 parts of phenyl xylyl ethane (produced by JX Nippon Oil & Energy Corp., product name "Hisol SAS-296") and 100 parts of a 1% aqueous polyvinyl alcohol solution and stirred for 10 minutes with a dissolver at a revolution of 2000 rpm. Thereafter, 3 parts of dimethylpolysiloxane were added to the mixed solution and gently stirred for 3 hours at 60° C., thereby to obtain an agrochemical composition for foliage treatment containing the microencapsulated pyroxasulfone wherein the masking material is polyurea. This composition had spherical granules having an average particle size of 36 μm.

Example 16

To a mixture prepared by mixing 5 parts of pyroxasulfone and 2.5 parts of carnauba wax under heating for 1 hour at 90° C., 2 parts of sodium alkylnaphthalene sulfonate, 2 parts of polyoxyethylene alkylphenyl ether, 16 parts of white carbon, 18 parts of diatomaceous earth and 54.5 parts of clay were added and the resultant mixture was pulverized, thereby to obtain an agrochemical composition for foliage treatment containing pyroxasulfone coated with carnauba wax which is a masking material. This composition had irregular granules having an average particle size of 43 μm.

Example 17

To a mixture prepared by mixing 5 parts of pyroxasulfone and 25 parts of carnauba wax under heating for 1 hour at 90° C., 2 parts of sodium alkylnaphthalene sulfonate, 2 parts of polyoxyethylene alkylphenyl ether, 16 parts of white carbon, 18 parts of diatomaceous earth and 32 parts of clay were added and the resultant mixture was pulverized, thereby to obtain an agrochemical composition for foliage treatment containing pyroxasulfone coated with carnauba wax which is a masking material. This composition had irregular granules having an average particle size of 21 μm.

Example 18

To a mixture prepared by mixing 5 parts of pyroxasulfone and 50 parts of carnauba wax under heating for 1 hour at 90° C., 2 parts of sodium alkylnaphthalene sulfonate, 2 parts of polyoxyethylene alkylphenyl ether, 16 parts of white carbon, 18 parts of diatomaceous earth and 7 parts of clay were added and the resultant mixture was pulverized, thereby to obtain an agrochemical composition for foliage treatment containing pyroxasulfone coated with carnauba wax which is a masking material. This composition had irregular granules having an average particle size of 38 μm.

Example 19

To a mixture prepared by mixing 5 parts of pyroxasulfone and 5 parts of a copolymer of acrylic acid ester and styrene under heating for 1 hour at 70° C., 2 parts of sodium alkylnaphthalene sulfonate, 2 parts of polyoxyethylene alkylphenyl ether, 16 parts of white carbon, 18 parts of diatomaceous earth and 52 parts of clay were added and the resultant mixture was pulverized, thereby to obtain an agrochemical composition for foliage treatment containing pyroxasulfone coated with the copolymer of acrylic acid ester and styrene which is a masking material. This composition had irregular granules having an average particle size of 23 μm.

Example 20

To a mixture prepared by mixing 5 parts of pyroxasulfone and 10 parts of a copolymer of acrylic acid ester and stylene under heating for 1 hour at 70° C., 2 parts of sodium alkylnaphthalene sulfonate, 2 parts of polyoxyethylene alkylphenyl ether, 16 parts of white carbon, 18 parts of diatomaceous earth and 47 parts of clay were added and the resultant mixture was pulverized, thereby to obtain an agrochemical composition for foliage treatment containing pyroxasulfone coated with the copolymer of acrylic acid ester and styrene which is a masking material. This composition had irregular granules having an average particle size of 63 μm.

Example 21

To a mixture prepared by mixing 5 parts of pyroxasulfone and 5 parts of a polyester resin under heating for 1 hour at 70° C., 2 parts of sodium alkylnaphthalene sulfonate, 2 parts of polyoxyethylene alkylphenyl ether, 16 parts of white carbon, 18 parts of diatomaceous earth and 52 parts of clay were added and the resultant mixture was pulverized, thereby to obtain an agrochemical composition for foliage treatment containing pyroxasulfone coated with the polyester which is a masking material. This composition had irregular granules having an average particle size of 67 μm.

Example 22

To a mixture prepared by mixing 5 parts of pyroxasulfone and 5 parts of a polyethyleneglycol-polyethylene terephthalate copolymer under heating for 1 hour at 70° C., 2 parts of sodium alkylnaphthalene sulfonate, 2 parts of polyoxyethylene alkylphenyl ether, 16 parts of white carbon, 18 parts of diatomaceous earth and 52 parts of clay were added and the resultant mixture was pulverized, thereby to obtain an agrochemical composition for foliage treatment containing pyroxasulfone coated with the polyethyleneglycol-polyethylene terephthalate copolymer which is a masking material. This composition had irregular granules having an average particle size of 44 μm.

Example 23

To a mixture prepared by mixing 5 parts of pyroxasulfone, 15 parts of carnauba wax and 1 part of hybrid silicone powder (produced by Shin-Etsu Chemical Co., Ltd., product name "KMP-601") under heating for 1 hour at 90° C., 2 parts of sodium alkylnaphthalene sulfonate, 2 parts of polyoxyethylene alkylphenyl ether, 16 parts of white carbon, 18 parts of diatomaceous earth and 41 parts of clay were added and the resultant mixture was pulverized, thereby to obtain an agrochemical composition for foliage treatment containing pyroxasulfone coated with carnauba wax which is a masking material. This composition had irregular granules having an average particle size of 21 μm.

Example 24

To a mixture prepared by mixing 5 parts of pyroxasulfone, 25 parts of carnauba wax and 2.5 parts of silicone rubber powder (produced by Shin-Etsu Chemical Co., Ltd., product name "KMP-597") under heating for 1 hour at 90° C., 2 parts of sodium alkylnaphthalene sulfonate, 2 parts of polyoxyethylene alkylphenyl ether, 16 parts of white carbon, 18 parts of diatomaceous earth and 29.5 parts of clay were added and the resultant mixture was pulverized, thereby to obtain an agrochemical composition for foliage treatment containing pyroxasulfone coated with carnauba wax which is a masking material. This composition had irregular granules having an average particle size of 26 μm.

Comparative Example 1

50 Parts of pyroxasulfone, 3 parts of sodium alkylnaphthalene sulfonate, 2 parts of polyoxyethylene alkylphenyl ether, 5 parts of sodium lignin sulfonate, 18 parts of diatomaceous earth and 22 parts of clay were added. The resultant mixture was pulverized and admixed with an appropriate volume of water for kneading followed by extrusion granulation by using an extrusion granulator through a screen of 0.7 mm mesh opening diameter and particle size assorting was followed by drying at a material temperature of 60° C. and screening, thereby to obtain an agrochemical composition for foliage treatment containing pyroxasulfone.

Test Example 1

Evaluation Test on Phytotoxicity to *Glycine max* by Foliage Treatment

Upland soil was filled in a plastic pot of 11 cm each in length, width, and height and seeds of *Glycine max* were sowed on it and covered with soil. Then, *Glycine max* plants were grown from the seeds and, when the *Glycine max* plants reached a period when the first two true leaves were fully expanded, each of the agrochemical compositions for foliage treatment obtained in Examples 7, 8, 9, 10 and 11 and Comparative Example 1 was taken by weighing in an amount corresponding to 210 g of pyroxasulfone per one hectare, diluted with water and then applied for foliage spraying at a spray water volume of 200 L per one hectare over the Glycine max plants in a uniform manner by using a small sprayer. Subsequently, the plants were grown in a greenhouse and examined by observation 16 days after the treatment. In the examination, an experimental group consisting of untreated plants was used as a control group and the degree of phytotoxicity was evaluated according to the criteria as shown in Table 1 and represented with an index from 0 to 10 in an 11-point grading system. The result of the examination is shown in Table 2.

TABLE 1

| Index | Herbicidal effect and degree of phytotoxicity in portions above soil level |
|---|---|
| 0 | Growth inhibition equivalent to the control group but less than 10% growth inhibition |
| 1 | not less than 10% but less than 20% growth inhibition |
| 2 | not less than 20% but less than 30% growth inhibition |
| 3 | not less than 30% but less than 40% growth inhibition |
| 4 | not less than 40% but less than 50% growth inhibition |
| 5 | not less than 50% but less than 60% growth inhibition |
| 6 | not less than 60% but less than 70% growth inhibition |
| 7 | not less than 70% but less than 80% growth inhibition |
| 8 | not less than 80% but less than 90% growth inhibition |
| 9 | not less than 90% but less than 100% growth inhibition |
| 10 | 100% growth inhibition (complete withering) |

TABLE 2

| | Dosage of pyroxasulfone (g/ha) | Index of phytotoxicity to *Glycine max* (16 days after treatment) |
|---|---|---|
| Example 7 | 210 | 0 |
| Example 8 | 210 | 0 |
| Example 9 | 210 | 0 |
| Example 10 | 210 | 0 |
| Example 11 | 210 | 0 |
| Comparative Example 1 | 210 | 2 |

Test Example 2

Evaluation Test on Phytotoxicity to Cotton Plants by Foliage Treatment

Upland soil was filled in a plastic pot of 11 cm each in length, width, and height and seeds of cotton plants were sowed on it and covered with soil. Then, cotton plants were grown from the seeds and, when the cotton plants reached a period when the first two true leaves were fully expanded, each of the agrochemical compositions for foliage treatment obtained in Examples 7, 8, 9, 10 and 11 and Comparative Example 1 was taken by weighing in an amount corresponding to 125 g of pyroxasulfone per one hectare, diluted with water and then applied for foliage spraying at a spray water volume of 200 L per one hectare over the cotton plants in a uniform manner by using a small sprayer. Subsequently, the plants were grown in a greenhouse and examined by observation 17 days after the treatment. In the examination, an experimental group consisting of untreated plants was used as a control group and the degree of phytotoxicity was evaluated according to the criteria as shown in Table 1 and represented with an index from 0 to 10 in an 11-point grading system. The result of the examination is shown in Table 3.

TABLE 3

| | Dosage of Pyroxasulfone (g/ha) | Index of phytotoxicity to cotton plants (17 days after treatment) |
|---|---|---|
| Example 7 | 125 | 0 |
| Example 8 | 125 | 0 |
| Example 9 | 125 | 0 |
| Example 10 | 125 | 0 |

TABLE 3-continued

| | Dosage of Pyroxasulfone (g/ha) | Index of phytotoxicity to cotton plants (17 days after treatment) |
|---|---|---|
| Example 11 | 125 | 0 |
| Comparative Example 1 | 125 | 2 |

Test Example 3

Evaluation Test on Phytotoxicity to *Sesamum indicum* by Foliage Treatment

Seeds of *Sesamum indicum* plants were sowed on a farm field and covered with soil. Then, *Sesamum indicum* plants were grown from the seeds and, when the *Sesamum indicum* reached a plant height of 15 cm, each of the agrochemical compositions for foliage treatment obtained in Examples 7, 9 and 10 and Comparative Example 1 was taken by weighing in an amount corresponding to 148 g of pyroxasulfone per one hectare, diluted with water and then applied to an area of 2 meters wide and 4.5 meters long for foliage spraying at a spray water volume of 200 L per one hectare over the *Sesamum indicum* plants in a uniform manner by using a backpack sprayer. Subsequently, the *Sesamum indicum* plants were further grown and examined by observation 5 days after the treatment. In the examination, an experimental group consisting of untreated plants was used as a control group and the degree of phytotoxicity was evaluated according to the criteria as shown in Table 1 and represented with an index from 0 to 10 in an 11-point grading system. The result of the examination is shown in Table 4.

TABLE 4

| | Dosage of Pyroxasulfone (g/ha) | Index of phytotoxicity to *Sesamum indicum* (5 days after treatment) |
|---|---|---|
| Example 7 | 148 | 0 |
| Example 9 | 148 | 1 |
| Example 10 | 148 | 0 |
| Comparative Example 1 | 148 | 2 |

Test Example 4

Evaluation Test on Herbicidal Effect on Weeds by Soil Treatment at Upland Soil

Upland soil was filled in a plastic pot of 11 cm each in length, width, and height and seeds of *Echinochloa crus-galli* var. *caudata* were sowed on it and covered with soil. Then, each of the agrochemical compositions for foliage treatment obtained in Examples 7, 9, 10 and 11 and Comparative Example 1 was taken by weighing in an amount corresponding to 50 g of pyroxasulfone per one hectare, diluted with water and then applied on the surface of the soil at a spray water volume of 200 L per one hectare in a uniform manner by using a small sprayer. Subsequently, the plants were grown in a greenhouse and examined by observation 14 days after the treatment. In the examination, an experimental group consisting of untreated plants was used as a control group and the degree of herbicidal effect was evaluated according to the criteria as shown in Table 1 and represented with an index from 0 to 10 in an 11-point grading system. The result of the examination is shown in Table 5.

TABLE 5

| | Dosage of Pyroxasulfone (g/ha) | Index of herbicidal effect (14 days after treatment) |
|---|---|---|
| Example 7 | 50 | 9 |
| Example 9 | 50 | 10 |
| Example 10 | 50 | 9 |
| Example 11 | 50 | 10 |
| Comparative Example 1 | 50 | 9 |

Test Example 5

Evaluation Test on Phytotoxicity to Genetically Modified Crops when Using Agrochemical Active Ingredients in Combination Roundup ready flex cotton (produced by Monsant Co.) (a cotton variety having tolerance to glyphosate conferred by gene recombination technology) was used for the test. Seeds of the cotton plants were sowed in the furrow of 0.96 meter on a farm field and covered with soil. Then, the cotton plants were grown from the seeds and, when the cotton plants reached a period when the first three true leaves were fully expanded, each of the agrochemical compositions for foliage treatment obtained in Examples 7, 9 and 10 and Comparative Example 1, which was taken by weighing in an amount corresponding to 105 g of pyroxasulfone per one hectare, and a glyphosate formulation (produced by Monsant Co., product name "Roundup PowerMAX") which was taken by weighing in an amount corresponding to 1070 g of glyphosate per one hectare were diluted with water and then applied to an area of 2 meters wide and 4.5 meters long for foliage spraying at a spray water volume of 200 L per one hectare over the cotton plants in a uniform manner by using a backpack sprayer. Subsequently, the cotton plants were further grown and examined by observation 14 days after the treatment. In the examination, an experimental group consisting of untreated plants was used as a control group and the degree of phytotoxicity was evaluated according to the criteria as shown in Table 1 and represented with an index from 0 to 10 in an 11-point grading system. The result of the examination is shown in Table 6.

TABLE 6

| | Dosage of Pyroxasulfone (g/ha) | Index of phytotoxicity to cotton plants (14 days after treatment) |
|---|---|---|
| Composition of Example 7 and glyphosate | 105 | 1 |
| Composition of Example 9 and glyphosate | 105 | 1 |
| Composition of Example 10 and glyphosate | 105 | 1 |
| Composition of Comparative Example 1 and glyphosate | 105 | 3 |

Test Example 6

Evaluation Test 2 on Phytotoxicity to Genetically Modified Crops when Using Agrochemical Active Ingredients in Combination LibertyLink cotton (produced by Bayer CropScience) (a cotton variety having tolerance to glufosinate conferred by gene recombination technology) was used for the test. Seeds of the cotton plants were sowed in the furrow of 0.96 meter on a farm field and covered with soil. Then, the cotton plants were grown from the seeds and, when the cotton plants reached a period when the first three true leaves were fully expanded, each of the agrochemical compositions for foliage treatment obtained in Examples 7, 9 and 10 and Comparative Example 1, which was taken by weighing in an amount corresponding to 105 g of pyroxasulfone per one hectare, and a glufosinate formulation (produced by Bayer CropScience, product name "Ignite") which was taken by weighing in an amount corresponding to 593 g of glyphosate per one hectare were diluted with water and then applied to an area of 2 meters wide and 4.5 meters long for foliage spraying at a spray water volume of 200 L per one hectare over the cotton plants in a uniform manner by using a backpack sprayer. Subsequently, the cotton plants were further grown and examined by observation 14 days after the treatment. In the examination, an experimental group consisting of untreated plants was used as a control group and the degree of phytotoxicity was evaluated according to the criteria as shown in Table 1 and represented with an index from 0 to 10 in an 11-point grading system. The result of the examination is shown in Table 7.

TABLE 7

| | Dosage of Pyroxasulfone (g/ha) | Index of phytotoxicity to cotton plants (14 days after treatment) |
|---|---|---|
| Composition of Example 7 and glufosinate | 105 | 0 |
| Composition of Example 9 and glufosinate | 105 | 0 |
| Composition of Example 10 and glufosinate | 105 | 0 |
| Composition of Comparative Example 1 and glufosinate | 105 | 2 |

Test Example 7

Dissolution Test

Each of the agrochemical compositions for foliage treatment, which had been obtained in Examples 7, 9, 10, 11, 12, 13, 14, 15, 16 and 18 and Comparative Example 1, in an amount corresponding to 8.5 mg of pyroxasulfone was added to 40 mL of distilled water in a glass screw neck vial having a volume of 50 mL and, after shaking well, left to stand under the temperature condition of 20° C. Aliquots of the water were withdrawn 1 hour, 3 hours, 6 hours and 24 hours after the mixture was left to stand, and the concentration of pyroxasulfone in water was measured for each aliquot by HPLC analysis. The result is shown in Table 8.

TABLE 8

| | Concentration of pyroxasulfone in water (ppm) | | | |
|---|---|---|---|---|
| | After 1 hour | After 3 hours | After 6 hours | After 24 hours |
| Example 7 | 1.5 | 2.8 | 3.3 | 3.5 |
| Example 9 | 2.6 | 4.0 | 4.5 | 4.9 |
| Example 10 | 1.9 | 3.2 | 3.6 | 4.3 |
| Example 11 | 1.6 | 2.7 | 3.3 | 4.0 |
| Example 12 | 1.2 | 2.3 | 3.0 | 3.2 |
| Example 13 | 0.5 | 1.2 | 1.8 | 2.4 |
| Example 14 | 0.9 | 1.1 | 1.4 | 2.1 |
| Example 15 | 0.6 | 0.6 | 0.8 | 1.8 |
| Example 16 | 1.6 | 2.7 | 3.3 | 4.1 |
| Example 18 | 0.8 | 1.6 | 2.4 | 4.1 |
| Comparative Example 1 | 6.3 | 6.8 | 6.7 | 6.6 |

The invention claimed is:

1. An agrochemical composition for foliage treatment comprising pyroxasulfone and a masking material that masks the pyroxasulfone, wherein the pyroxasulfone is microencapsulated in or coated with the masking material such that phytotoxicity to a cultivated crop due to adhesion thereto when foliage spraying is performed is avoided, wherein the masking effect of the masking material is quickly diminished after the spraying and wherein a concentration $K_{24}$ is equal to or less than twice a solubility of pyroxasulfone in water and a concentration $K_1$ is equal to or less than 55% of the concentration $K_{24}$, wherein the concentrations $K_1$ and $K_{24}$ are obtained by measuring a concentration of pyroxasulfone in water 1 hour and 24 hours after a pre-determined amount of the agrochemical composition for foliage treatment is added to water at 20° C., respectively.

2. The agrochemical composition for foliage treatment according to claim 1, wherein crystal particles of the pyroxasulfone are directly coated with the masking material.

3. The agrochemical composition for foliage treatment according to claim 1, wherein pyroxasulfone is microencapsulated by being enclosed or included in the wall member of the masking material.

4. The agrochemical composition for foliage treatment according to claim 1, wherein the masking material has an average particle size in the range of 0.1 to 150 μm.

5. The agrochemical composition for foliage treatment according to claim 1, wherein a ratio of the masking material to the pyroxasulfone is in the range of 0.1 to 50 parts by mass relative to 1 part by mass of the pyroxasulfone.

6. The agrochemical composition for foliage treatment according to claim 1, wherein the masking material is selected from the group consisting of polyurea, polyurethane, polyamide, polyester, ethylcellulose, poly(meth)acrylate-based copolymers, carnauba wax, montanic ester wax, hardened oils and fats, polylactic acid, gelatin, cross-linked melamine, polystyrene, polystyrene-based copolymers, wax, yeast cell wall, alginate, polyglycolic acid, polyethylene glycol-based copolymers and shellac.

7. The agrochemical composition for foliage treatment according to claim 1, which is in a dosage form of a dust powder, granule, wettable powder, water-dispersible granule, aqueous suspension concentrate, or oil-based suspension concentrate.

8. The agrochemical composition for foliage treatment according to claim 1, which further comprises an agrochemical active ingredient other than pyroxasulfone.

9. The agrochemical composition for foliage treatment according to claim 8, wherein the agrochemical active ingredient other than pyroxasulfone is glyphosate or glufosinate.

10. A method of performing foliage treatment, comprising combining the agrochemical composition for foliage treatment according to claim 1 with an agrochemical active ingredient other than pyroxasulfone and performing a foliage treatment.

11. A method of controlling a pest, comprising spraying the agrochemical composition for foliage treatment according to claim 1 on foliage over an upland field where a cultivated crop in the growing period thereof is growing.

12. The method for controlling a pest according to claim 11, wherein the cultivated crop is selected from the group consisting of *Triticum aestivum, Hordeum vulgare, Secale cereale, Zea mays, Sorghum bicolor, Glycine max, Brassica rapa, Carthamus tinctorius, Helianthus annuus, Linum usitatissimum, Arachis hypogaea, Sesamum indicum, Solanum tuberosum, Ipomoea batatas, Allium cepa, Allium sativum, Beta vulgaris*, cotton plants, mint plants, and lawn plants.

* * * * *